US010123964B2

(12) United States Patent
Wenzel et al.

(10) Patent No.: US 10,123,964 B2
(45) Date of Patent: Nov. 13, 2018

(54) TOPICAL COMPOSITION INCLUDING A COMBINATION OF EXTRACTS FOR REDUCING SIGNS OF SKIN AGING

(71) Applicant: Kimberly-Clark Worldwide, Inc., Neenah, WI (US)

(72) Inventors: Scott W. Wenzel, Neenah, WI (US); David J. Tyrrell, Milwaukee, WI (US); Alencia Vanay Grice, Roswell, GA (US); Stephanie VandeVen Teat, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 43 days.

(21) Appl. No.: 15/306,192

(22) PCT Filed: Apr. 30, 2014

(86) PCT No.: PCT/US2014/036194
§ 371 (c)(1),
(2) Date: Oct. 24, 2016

(87) PCT Pub. No.: WO2015/167539
PCT Pub. Date: Nov. 5, 2015

(65) Prior Publication Data
US 2017/0042794 A1  Feb. 16, 2017

(51) Int. Cl.
| | | |
|---|---|---|
| *A61K 36/185* | (2006.01) |
| *A61K 36/22* | (2006.01) |
| *A61K 8/97* | (2017.01) |
| *A61K 8/44* | (2006.01) |
| *A61Q 19/00* | (2006.01) |
| *A61Q 19/08* | (2006.01) |
| *A61K 8/63* | (2006.01) |
| *A61Q 19/10* | (2006.01) |

(52) U.S. Cl.
CPC .............. *A61K 8/97* (2013.01); *A61K 8/44* (2013.01); *A61K 8/63* (2013.01); *A61Q 19/00* (2013.01); *A61Q 19/007* (2013.01); *A61Q 19/08* (2013.01); *A61K 2800/596* (2013.01); *A61K 2800/74* (2013.01); *A61Q 19/10* (2013.01)

(58) Field of Classification Search
CPC .............................. A61K 36/185; A61K 36/22
USPC .................................................... 424/777, 735
See application file for complete search history.

(56) References Cited

U.S. PATENT DOCUMENTS

| | | | |
|---|---|---|---|
| 6,406,720 B1 * | 6/2002 | Pauly ....................... A61K 8/97 424/401 |
| 2002/0028227 A1 | 3/2002 | Yu et al. | |
| 2004/0161435 A1 | 8/2004 | Gupta | |
| 2009/0012049 A1 | 1/2009 | Fabre et al. | |
| 2010/0099640 A1 | 4/2010 | Geuns et al. | |
| 2012/0107427 A1 | 5/2012 | Kim et al. | |

FOREIGN PATENT DOCUMENTS

| | | |
|---|---|---|
| CN | 101756847 A | 6/2010 |
| FR | 2962330 A1 | 1/2012 |
| JP | 2006249051 A | 9/2006 |
| JP | 2006298814 A | 11/2006 |
| JP | 2007161589 A | 6/2007 |
| WO | 2012145609 A1 | 10/2012 |
| WO | 2013149323 A1 | 10/2013 |

OTHER PUBLICATIONS

Song et al. "Protective effect of mango (*Mangifera indica* L.) against UVB-induced skin aging in hairless mice", Photodermatology, photoimmunology and photomedicine, Apr. 2013, vol. 29, No. 2, pp. 84-89.
International Search Report and Written Opinion for Application PCT/US2014/036188, dated Feb. 6, 2015, 11 pages.
International Preliminary Report on Patentability for Application PCT/US2014/036188, dated Apr. 21, 2016, 6 pages.
International Search Report and Written Opinion for Application PCT/US2014/036194, dated Feb. 29, 2016, 9 pages.

* cited by examiner

*Primary Examiner* — Christopher R Tate
*Assistant Examiner* — Deborah A Davis
(74) *Attorney, Agent, or Firm* — Armstrong Teasdale LLP

(57) ABSTRACT

Compositions for reducing skin aging are disclosed herein. The compositions can be topically applied to a skin region to reduce or prevent skin wrinkles, fine lines, thinning skin, sagging skin, skin dryness, and skin itchiness.

20 Claims, 9 Drawing Sheets

Negative Control

Positive Control

Adipofill'in

Ecobidens

Ecosamba

Kombuchka

Negative Control

Positive Control

Adipofill'in

Ecobidens

Ecosamba

Kombuchka 0.5% Adipofill'in  0.5% Ecosamba  0.5% Adipofill'in 0.5% Ecosamba

TOPICAL COMPOSITION INCLUDING A COMBINATION OF EXTRACTS FOR REDUCING SIGNS OF SKIN AGING

BACKGROUND OF THE DISCLOSURE

The present disclosure relates generally to compositions and methods to reduce the signs of skin aging of the face and body. More particularly, the present disclosure relates to compositions including a combination of extracts and methods of topically applying the compositions for stimulating adipogenesis and lipogenesis to reduce signs of skin aging.

Human skin changes drastically with age, becoming thinner and drier due to thinning of the epithelial layer and degeneration of the underlying fat and connective tissue. Other signs of aged skin include loss of skin volume, loss of skin elasticity, firmness and resiliency.

The skin of the face and body areas are particularly prone to signs of aging. Signs of aging that affect the skin of the face and body include, for example, wrinkles, fine lines, thinning skin, sagging skin, sinking skin, skin dryness, and skin itchiness.

Changes in hormonal status (e.g., decrease in estrogen levels, increase in follicle-stimulating hormone (FSH) levels) during perimenopause and menopause can make changes in the skin even more pronounced. Atrophic manifestations associated with menopause such as skin thinning and the accompanying functional decrease in skin "strength" are systemic. In particular, there is a marked decrease in collagen I and collagen III and a decrease in size and number of adipocytes in aged skin. These effects result in skin areas, and in particular, facial skin, neck skin, chest skin, breast skin, hand skin, leg skin, and feet skin, showing increased signs of aging (e.g., wrinkles, fine lines, sagging skin, thinning skin, etc.).

Vulvar skin and the labia are particular additional skin regions that change as a woman ages, especially as a result of the changes in hormone levels and following menopause. Vulvar skin and the labia can lose elasticity as a result of the degeneration of underlying fat and connective tissues, a loss of collagen and thinning of the epithelial layer of the skin. The vulvar skin can also become less moist. The loss of elasticity and moisture of the mucosal vulvar skin can diminish the youthful look of the vulvar anatomy. A woman can become ashamed and even depressed about the toll that aging takes on the appearance of her outer genitalia as a result of changes of the vulvar skin and labia.

A wide variety of creams and lotions exist that can cosmetically improve the appearance, and sometimes, the structure of the skin on the face and body. Such compositions often employ retinoids, hydroxy acids and/or exfoliants to encourage skin rejuvenation, increase firmness or otherwise cosmetically improve the skin. Many cosmetic products provide moisture and can enhance the skin's appearance by plumping the skin using irritants that cause inflammation. Further, there are known active cosmetic ingredients that claim to enhance adipogenesis, however, their potency is variable and therefore has not been shown to be effective for this use. Other cosmetic products are available that claim to rejuvenate and create a more youthful appearance by targeting extracellular matrix proteins such as elastin and collagen, which are produced by fibroblasts. These compositions can be inappropriate for use on the delicate mucous membrane of the vulva and labia. Incompatibility with mucosal skin necessitates alternative cosmetic creams and lotions specifically designed for application to reduce the effects of aging of the vulvar skin and labia.

Medical procedures, such as dermal injections and reconstructive surgery, are also available to reduce the signs of aging. Cosmetic surgery has recently grown in popularity to aesthetically enhance the appearance of skin and even the appearance of the skin of the vulva and labia. These procedures, however, are not always desirable options as surgery can be costly, painful and very invasive.

While the cosmetic products and medical procedures described above are suitable for treating aged skin of the face and body and aging of the vulvar skin and labia, alternative compositions and methods for improving skin are desirable. Accordingly, there exists a need to develop alternative compositions and methods for improving the overall fullness and appearance of aging skin of the face and body and aging of the vulvar skin and labia. It would be highly advantageous if the compositions and methods could be topically applied such that invasive, painful, and costly medical procedures could be avoided.

BRIEF DESCRIPTION OF THE DISCLOSURE

The present disclosure is generally directed to compositions and methods to reduce the signs of skin aging. Particularly, in one aspect, the present disclosure is directed to a topical composition comprising: a first formulation comprising L-ornithine and a second formulation comprising *Spondias mombin* pulp extract, *Mangifera indicia* (Mango) pulp extract and *Musa sapientum* (banana) pulp extract.

In another aspect, the present disclosure is directed to a topical composition comprising: a first formulation comprising propanediol, L-ornithine, phospholipids, and glycolipids, and a second formulation comprising water, glycerin, *Spondias mombin* pulp extract, *Mangifera* indicia pulp extract, *Musa sapientum* pulp extract, benzyl alcohol, and potassium sorbate.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
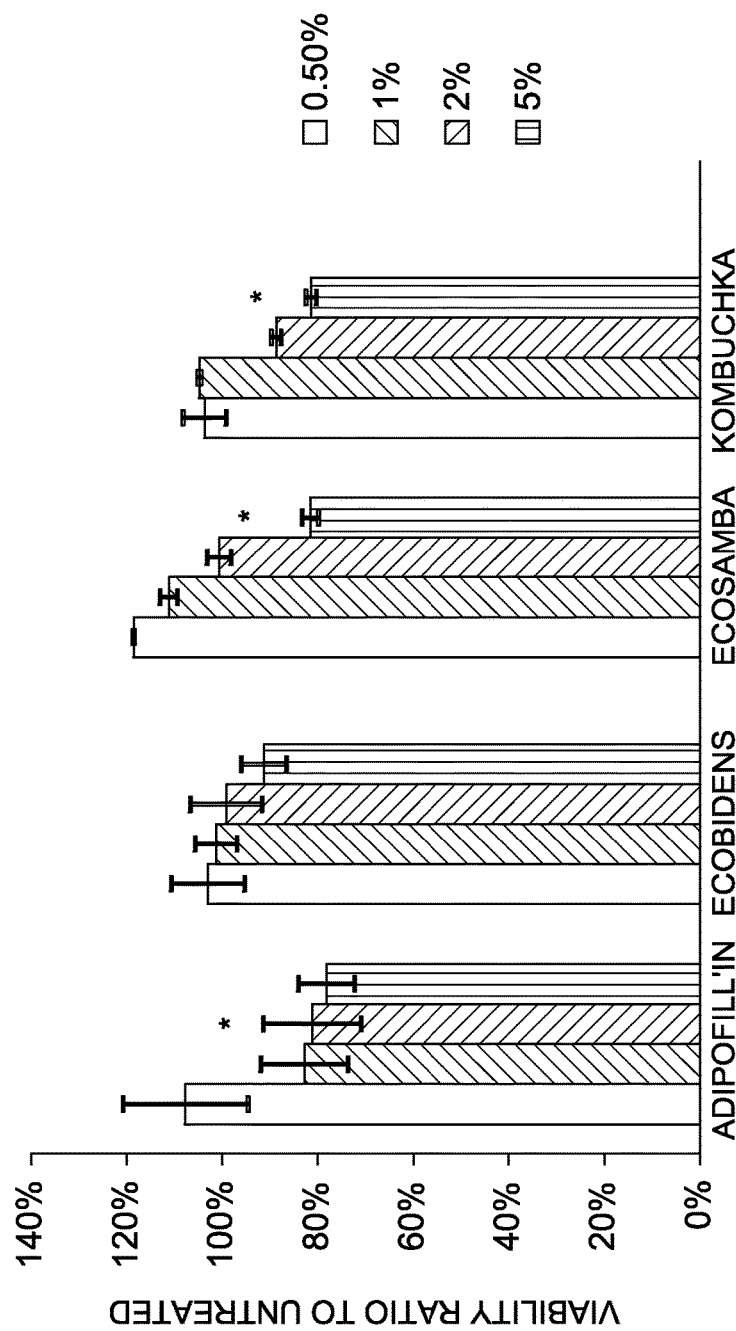
FIG. 1 is a graphical illustration showing cell survival following treatment of cells with various active ingredients, as discussed in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, compositions and methods have been discovered that surprisingly allow for reducing the signs of skin aging. The methods of the present disclosure have a broad and significant impact, as they increase adipocyte size and number ("adipogenesis") and lipid production ("lipogenesis") to result in a more youthful appearance of aged skin of the face and body. More particularly, as used herein, the term "adipogenesis" refers to increased proliferation of adipocytes and/or increased differentiation of adipose-derived stem cells. Increasing adipocyte cell size and number and/or lipid production within adipocytes can reduce the signs of skin aging, including counteracting skin thinning, increasing overall fullness, increasing skin firmness and increasing skin resiliency.

As used herein, "body" refers to an individual's entire body, and particularly, includes the regions of the face (including forehead, cheeks, chin, and eyelids), neck, shoulders, breast, chest, legs, hands, feet and vulvar area including vulvar skin, for example, the vulva, labia, labia majora, labia minor, mons pubis, vulval vestibule, and combinations thereof.

Compositions
Active Ingredients/Extracts

The present disclosure has unexpectedly found that particular extracts can be topically applied, alone or in combination, to an individual's skin as active ingredients in compositions to reduce the signs of skin aging. Particularly, the active ingredients of the compositions have been unexpectedly found to increase adipogenesis and/or lipogenesis, thereby increasing the number and size of adipocytes in subcutaneous adipose tissue found directly below the skin. This provides the user with plumper, fuller skin and a more youthful, smoother skin appearance.

In one aspect, the present disclosure is directed to compositions for reducing the signs of skin aging of the face and body. The composition includes a synergistic composition of active ingredients including a first formulation including L-ornithine and a second formulation including *Spondias mombin* pulp extract, *Mangifera indicia* (Mango) pulp extract and *Musa sapientum* (banana) pulp extract. A suitable first formulation can be, for example, propanediol, L-ornithine, phospholipids and glycolipids (such as commercially available ADIPOFILL'IN™ from Lucas Meyer Cosmetics (Quebec, Canada). A suitable second formulation includes water, glycerin, *Spondias mombin* pulp extract, *Mangifera indicia* (Mango) pulp extract, *Musa sapientum* (banana) pulp extract, benzyl alcohol, and potassium sorbate (this formulation is referred to herein as "ECOSAMBA"). A particularly suitable second formulation can be ECOSAMBA PRO (commercially available from Chemyunion Quimica LTDA; Sorocaba, Brazil), which includes as active ingredients, from about 7.5% (w/w) to about 30% (w/w) *Spondias mombin* pulp extract, from about 5% (w/w) to about 30% (w/w) *Mangifera indica* (Mango) pulp extract, and about 1% (w/w) to about 20% (w/w) *Musa sapientum* (Banana) pulp extract. As used herein, "w/w" refers to the amount of a component "by weight of the composition".

It has been surprisingly found that the combination of the first formulation and the second formulation functions synergistically to plump the skin by increasing the number and size of the adipocytes in subcutaneous adipose tissue found directly below the skin. Without being bound by theory, is believed that the first formulation induces fat refilling of adipocytes, while the second formulation has a lipogenic effect, thereby enhancing adipocytes.

Suitable amounts of the first formulation in the composition can include from about 0.1% (w/w) to about 20% (w/w), including from about 0.15% (w/w) to about 10% (w/w), including from about 0.2% (w/w) to about 5% (w/w), and including from about 0.25% (w/w) to about 2% (w/w). Suitable amounts of the second formulation ("ECOSAMBA") in the composition can include from about 0.1% (w/w) to about 20% (w/w), including from about 0.15% (w/w) to about 10% (w/w), including from about 0.2% (w/w) to about 5% (w/w), and including from about 0.25% (w/w) to about 2% (w/w).

Particularly, as shown in the Examples below, it has been unexpectedly found that the combination of the first and second formulations behaved synergistically in increasing adipogensis and lipogenesis; that is, the combination improved these effects better than either formulation alone, and even better than what would be expected additively when the two formulations are used together.

Additional Optional Ingredients

The compositions described herein can further include additional ingredients and optional ingredients.

Generally, the compositions include a carrier with the active ingredient(s).

In one embodiment, for example, when the composition is to be applied to the vulvar region of an individual, the composition includes the active ingredient(s) and a hydrophilic carrier, a hydrophilic thickener, and/or a penetration enhancer. Suitable hydrophilic carriers can be, for example, water, alcohols, glycerin, glycerin derivatives, glycols, water-soluble emollients, and combinations thereof. Suitable examples of alcohols could include, but are not to be limited to, ethanol and isopropyl alcohol. Suitable examples of glycerin derivatives could include, but are not to be limited to, PEG-7 glyceryl cocoate. Suitable glycols could include, but are not to be limited to, propylene glycol, butylene glycol, pentylene glycol, ethoxydiglycol, dipropylene glycol, propanediol, and PEG-8. Suitable examples of water-soluble emollients could include, but are not to be limited to, PEG-6 Caprylic Capric Glycerides, Hydrolyzed Jojoba Esters, and PEG-10 Sunflower Glycerides.

In particularly suitable embodiments, the compositions are liquid compositions desirably containing water as the carrier. Suitable amounts of water can be from about 0.1% by weight of the composition to about 99.9% by weight of the composition. More typically, the amount of water can be from about 40% by weight of the composition to about 99.9% by weight of the composition. Preferably, the amount of water can be from about 60% by weight of the composition to about 99.9% by weight of the composition.

In another embodiment, the composition includes the active ingredient(s) and a hydrophobic carrier. Suitable hydrophobic carriers can be, for example, natural oils, synthetic oils and combinations thereof.

The topical compositions described herein can further include a skin penetrating enhancer or a mixture of skin penetration enhancers. A skin penetrating enhancer allows for the composition to pass through the epidermal layer and the dermal layer of the skin to reach the adipose tissue that underlies the skin wherein adipocytes are increased in number and/or size. This may be accomplished by a number of different mechanisms including, for example, by extracting lipids from the stratum corneum, increasing the partitioning of the active ingredients into the skin, and disrupting the lipid bilayer of the stratum corneum, thus rendering the stratum corneum structure more fluid and increasing the ability of the first and second formulations including the active ingredients to diffuse through the stratum corneum.

Suitable skin penetrating enhancers can be, for example, sulfoxides, alcohols, fatty acids, fatty acid esters, polyols, amides, surfactants, terpenes, alkanones, and organic acids, among others. Specific examples of suitable sulfoxides include dimethylsulfoxide (DMSO) and decylmethylsulfoxide, among others. Suitable alcohols include alkanols such as ethanol, propanol, butanol, pentanol, hexanol, octanol, n-octanol, nonanol, decanol, 2-butanol, 2-pentanol, and benzyl alcohol; fatty alcohols, such as caprylic alcohol, decyl alcohol, lauryl alcohol, 2-lauryl alcohol, myristyl alcohol, cetyl alcohol, stearyl alcohol, oleyl alcohol, linoleyl alcohol, and linolenyl alcohol; and isopropyl alcohol. Examples of suitable fatty acids include linear fatty acids such as valeric acid, heptanoic acid, pelagonic acid, caproic acid, capric acid, lauric acid, myristic acid, stearic acid, oleic acid, and caprylic acid; and branched fatty acids, such as isovaleric acid, neopentanoic acid, neoheptanoic acid, neononanoic acid, trimethyl hexanoic acid, neodecanoic acid, and isostearic acid. Examples of suitable fatty acid esters include aliphatic fatty acid esters such as isopropyl n-butyrate, isopropyl n-hexanoate, isopropyl n-decanoate, isopropyl myristate, isopropyl palmitate, and octyldodecyl myristate; alkyl fatty acid esters such as ethyl acetate, butyl acetate, methyl acetate, methylvalerate, methylpropionate, diethyl sebacate, and ethyl oleate; and diisopropyl adipate and dimethyl isosorbide. Examples of suitable polyols include propylene glycol, butylene glycol, polyethylene glycol, ethylene glycol, diethylene glycol, triethylene glycol, dipropylene glycol, ethoxydiglycol, pentylene glycol, glycerol, propanediol, butanediol, pentanediol, hexanetriol, and glycerin. Examples of suitable amides include urea, dimethylacetamide, diethyltoluamide, dimethylformamide (DMF), dimethyloctamide, dimethyldecamide, biodegradable cyclic urea (e.g., 1-alkyl-4-imidazoline-2-one), pyrrolidone derivatives, biodegradable pyrrolidone derivatives (e.g., fatty acid esters of N-(2-hydroxyethyl)-2-pyrrolidone), cyclic amides, hexamethylenelauramide and its derivatives, diethanolamine, and triethanolamine. Examples of pyrrolidone derivatives include 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone, and N-methylpyrrolidone. Examples of cyclic amides include 1-dodecylazacycloheptane-2-one (e.g., Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyldodecyl)azacyclohaptane-2-one, 1-geranylazacyclohexane-2-one, 1-geranylazacyclopentan-2,5-dione, and 1-farnesylazacyclopentan-2-one.

Typically, the compositions of the present disclosure include from about 0.01% (by weight of the composition) to about 25% (by weight of the composition) of a skin penetration enhancer, including from about 1% (by weight of the composition) to about 15% (by weight of the composition) of a skin penetration enhancer, and including from about 2% (by weight of the composition) to about 10% (by weight of the composition) of a skin penetration enhancer.

Optionally, the topical compositions may be formulated with a polar co-solvent to further increase the permeability of the first and second formulations into the skin. Preferably, the polar co-solvent is fully miscible in the composition, and has a high affinity for the intercellular spaces in the stratum corneum. Without wishing to be bound by any particular theory, it is believed that polar co-solvents with such characteristics are driven by osmosis into the intercellular spaces in the stratum corneum, causing the stratum corneum to swell. In such a swollen state, the intercellular spaces are more liquid-like and disordered, which enables the first and second formulations of the topical composition to more easily diffuse through the stratum corneum.

Examples of suitable polar co-solvents for inclusion in the compositions of the present disclosure include glycerin, propanediol, ethanol, propylene glycol, butanol, isopropanol, propanol, dimethyl isosorbide, butylene glycol, polyethylene glycol, dipropylene glycol, ethoxydiglycol, pentylene glycol, and combinations thereof.

Typically, the compositions of the present disclosure include from about 1% (by weight of the composition) to about 99% (by weight of the composition) of a polar co-solvent, including from about 1% (by weight of the composition) to about 75% (by weight of the composition) of a polar co-solvent, including from about 1% (by weight of the composition) to about 50% (by weight of the composition) of a polar co-solvent, including from about 1.5% (by weight of the composition) to about 25% (by weight of the composition) of a polar co-solvent, including from about 2% (by weight of the composition) to about 15% (by weight of the composition) of a polar co-solvent, and including from about 2.5% (by weight of the composition) to about 10% (by weight of the composition) of a polar co-solvent.

In some embodiments, the compositions can further include beta-sitosterol. It is believed that in combination with the first formulation and the second formulation, beta-sitosterol further reduces signs of skin aging of the face and body by stimulating adipogenesis and lipogenesis, and further stimulating collagen, elastin and extracellular matrix production.

Suitable amounts of beta-sitosterol can be from about 0.001% by weight of the composition to about 10.0% by weight of the composition. More typically, the amount of beta-sitosterol can be from about 0.005% by weight of the composition to about 7.5% by weight of the composition. Even more suitable, the amount of beta-sitosterol can be from about 0.01% by weight of the composition to about 5.0% by weight of the composition.

The composition can further include other known collagen, elastin, and extracellular matrix-stimulating ingredients. Collagen is a protein found in the connective tissue of the skin and other tissues of the body. Suitable collagen enhancers can be, for example, vitamins such as ascorbic acid and derivatives thereof, peptides such as palmitoyl tripeptide-5, botanical extracts such as pomegranate or mushroom, and minerals such as hematite.

Elastin is a protein found in the connective tissue of the skin and other tissues of the body. Suitable elastin enhancers can be, for example, vitamins such as ascorbic acid and derivatives thereof, peptides such palmitoyl hexapeptide-12, botanical extracts such as kudzu, horsetail, rice, dill and rosemary, and minerals such as zinc and copper.

The compositions can further include a vasodilator. Vasodilators can increase the blood flow within the skin. Suitable vasodilators can be, for example, glyceryl trinitrate, resveratrol, caffeine, ginger extract, *ginseng* and other botanical extracts such as, for example, hawthorn, mint, ivy, coffee and tea.

The compositions can further include a skin soothing agent. As used herein, "skin soothing agent" refers to compounds that reduce or prevent skin irritation. Skin irritation can result from loss of moisture, a change in pH, sweat, contact dermatitis from perfumes, powders, laundry detergent from clothing, and other compounds. Skin soothing agents can reduce irritation by neutralizing an irritant, down-regulating inflammatory cascades in the skin, and/or providing a protective layer on the skin. Suitable skin soothing agents can be, for example, botanical extracts such as calendula, chamomile, aloe, comfrey, coneflower; active materials such as allantoin, bisabolol, panthenol, beta-glucan, colloidal oatmeal, and ingredient blends such as SYMCALMIN (INCI: butylene glycol, pentylene glycol, hydroxyphenyl propamidobenzoic acid; commercially available from Symrise (Holzmiden, Germany) and SEPI-CALM (INCI: sodium palmitoyl proline, *nymphaea alba* flower extract; commercially available from Seppic (Fairfield, N.J.).

The compositions can further include a humectant. Humectants can elevate the hydration of the skin, in particular the epidermis and the dermis. Suitable humectants can be, for example, glycerol, glycerin, lactic acid, urea, aloe vera, betaine, hyaluronic acid, propanediol, propylene glycol, butylene glycol, and combinations thereof.

The compositions can further include an emulsifier, and in particular, an emulsifier that creates liquid crystalline networks or liposomal networks. Suitable non-limiting exemplary emulsifiers include, for example, OLIVEM® 1000 (INCI: Cetearyl Olivate (and) Sorbitan Olivate; commercially available from HallStar Company (Chicago, Ill.)), Arlacel™ LC (INCI: Sorbitan Stearate (and) Sorbityl Laurate; commercially available from Croda (Edison, N.J.), CRYSTALCAST® MM (INCI: Beta Sitosterol (and) Sucrose Stearate (and) Sucrose Distearate (and) Cetyl Alcohol (and) Stearyl Alcohol; commercially available from MMP Inc. (South Plainfield, N.J.), UNIOX CRISTAL (INCI: Cetearyl Alcohol (and) Polysorbate 60 (and) Cetearyl Glucoside; commercially available from Chemyunion (Sao Paulo, Brazil). Other suitable emulsifiers include lecithin, hydrogenated lecithin, lysolecithin, phosphatidylcholine, phospholipids, and combinations thereof.

The compositions can further include a preservative to preserve the stability. Preservatives can also prevent the growth of microbial organisms in the compositions. Suitable preservatives are known in the art, and include, for example, methylparaben, phenoxyethanol, capryl glycol, glyceryl caprylate, benzoic acid, sorbic acid, gallic acid, propylparaben and combinations thereof.

The compositions can further include a pH adjuster to control/maintain the pH of the composition within the range of skin pH. A suitable pH range of the composition can be from about 3.5 to about 6.

The compositions can further include fragrances, scents, dyes, surfactants, rheology modifiers, film formers and other components known to be useful in personal care formulations.

Methods of Use

In another aspect, the present disclosure is directed to methods of using the compositions to reduce skin aging of an individual's face and body.

In one aspect, the present disclosure is directed to a method for reducing signs of skin aging of the face and body in an individual in need thereof. The method includes topically applying a synergistic composition of active ingredients including a first formulation including L-ornithine and a second formulation including *Spondias mombin* pulp extract, *Mangifera indicia* (Mango) pulp extract and *Musa sapientum* (banana) pulp extract to a target skin region of the individual. The target skin region can be, for example, facial skin, neck skin, breast skin, shoulder skin, chest skin, leg skin, hand skin, feet skin and combinations thereof.

In another aspect, the present disclosure is directed to a method for reducing signs of vulvar skin aging in an individual in need thereof. The method includes topically applying a synergistic composition of active ingredients including a first formulation including L-ornithine and a second formulation including *Spondias mombin* pulp extract, *Mangifera indicia* (Mango) pulp extract and *Musa sapientum* (banana) pulp extract to a target skin region of the individual. The target skin region can be, for example, vulvar skin region, for example, the vulva, labia, the labia majora, labia minor, mons pubis, vulval vestibule and combinations thereof and combinations thereof.

In another aspect, the present disclosure is directed to a method for increasing adipogenesis in an individual in need thereof. The method includes topically applying a synergistic composition of active ingredients including a first formulation including L-ornithine and a second formulation including *Spondias mombin* pulp extract, *Mangifera indicia* (Mango) pulp extract and *Musa sapientum* (banana) pulp extract to a target skin region of the individual. The target skin region can be, for example, facial skin, neck skin, breast skin and combinations thereof. The target skin region can also be, for example, vulvar skin, for example, the vulva, labia, labia majora, labia minor, mons pubis, vulval vestibule and combinations thereof.

In another aspect, the present disclosure is directed to a method for increasing lipogenesis in an individual in need thereof. The method includes topically applying a synergistic composition of active ingredients including a first formulation including L-ornithine and a second formulation including *Spondias mombin* pulp extract, *Mangifera indicia* (Mango) pulp extract and *Musa sapientum* (banana) pulp extract to a target skin region of the individual. The target skin region can be, for example, facial skin, neck skin, breast skin and combinations thereof. The target skin region can also be, for example, vulvar skin, for example, the vulva, labia, labia majora, labia minor, mons pubis, vulval vestibule and combinations thereof.

As used herein, an "individual in need" refers to an individual having skin showing visible signs of aging such as, for example, wrinkles, fine lines, thinning skin, sagging skin, skin dryness, skin itchiness, skin fragility, loss of skin elasticity, and combinations thereof. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein.

As used herein, the term "individual" refers to a male human or a female human. In certain embodiments, the individual is a postmenopausal female human.

The compositions used in the methods described herein can further include additional ingredients as described herein and other components known to be useful in personal care formulations.

The composition can be applied to the target skin region by any suitable delivery vehicle. For example, the composition can be applied as a lotion, as a wash, as a gel, as a salve, as an ointment, as a cream, as a solid stick and as a foam. Additionally, the composition can be applied with a wipe, with mitts and gloves, using an aerosol dispenser, using a pump spray, using a trigger spray and using a squeeze bottle.

The compositions can be applied daily, every other day, every couple of days, every week, every month, and every year, as desired. The compositions can be applied multiple times per day, multiple times per week and/or multiple times per month.

In some embodiments, the compositions of the present disclosure can be used with additional skin care compositions as part of a skin care regimen. For example, in facial treatment and care, users typically use multiple products for cleansing, toning, and treating the skin of the face. Accordingly, the first product comprises a first composition typically capable of providing a first benefit to a user, and the second product comprises a second composition typically capable of providing a second benefit to a user. In the present disclosure, it should be understood that at least one of the products of the regime includes the topical composition of the present disclosure, thereby providing the benefit of reducing signs of skin aging. In some embodiments, it should be understood by one skilled in the art, that while the first product and second product can independently provide any benefit known in the art of the particular care regimen, in each particular multi-product care regimen, the first product and second product may include different compositions and thus, provide different benefits to the user.

Furthermore, as with the first product and second product of the care regimen, if more than two products are used in the multi-product care regimen, such as third, fourth, and/or fifth products (and more products if more than five products are desired), it should be recognized that the additional products should include active ingredients, each independently being capable of providing additional benefits to a user.

In an alternative embodiment, the multi-product care regime can include more than two products and can be configured such to provide a multiple day regimen. Without being limiting, in one example, the multi-product care regimen provides skin care for multiple days and, as such, a first product includes, for example, a cleansing composition, a second product includes the anti-skin aging composition of the present disclosure, a third product includes the same cleansing composition as the first product, and a fourth product includes the same anti-skin aging composition as the second product.

Without being limiting, examples of additional compositions providing skin care benefits in addition to the anti-skin aging composition of the present disclosure can include compositions for cleansing, toning, treating, moisturizing, protecting, finishing, and the like.

When the additional composition is a cleansing composition, the cleansing composition may be in any form known in the art, such as, for example, hand soaps, body soaps, body washes, shampoos, surface cleaners, dish soaps, facial cleansers, hand washes, and the like. These types of cleansing compositions typically include at least one foaming agent, such as a surfactant. Although discussed herein primarily in terms of a surfactant, it should be understood that the cleansing compositions may comprise other cleansing agents, and need not comprise a surfactant. For example, in certain embodiments, the compositions may comprise a thickener, a swellable clay, a foaming agent (which may or may not comprise a surfactant (e.g., ethoxylated skin conditioning agents, solubilizers, and derivatized silicone polymers)), and optionally a solvent or other carrier. Examples of such compositions include, for example, lotions, creams, anti-microbial compositions, and the like.

Suitable surfactants for use in the cleansing composition include anionic surfactants, amphoteric surfactants, cationic surfactants, zwitterionic surfactants, non-ionic surfactants, and combinations thereof.

Suitable anionic surfactants include, for example, alkyl sulfates, alkyl ether sulfates, alkyl aryl sulfonates, alpha-olefin sulfonates, alkali metal or ammonium salts of alkyl sulfates, alkali metal or ammonium salts of alkyl ether sulfates, alkyl phosphates, silicone phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, sulphosuccinates (e.g., sodium dioctylsulphosuccinate), and combinations thereof. Specific examples of anionic surfactants include sodium lauryl sulphate, sodium lauryl ether sulphate, ammonium lauryl sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauroyl isethionate, sodium N-lauryl sarcosinate, and combinations thereof.

Suitable cationic surfactants include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behenyltrimonium chloride, stearlkonium chloride, distearalkonium chloride, chlorohexidine diglutamate, polyhexamethylene biguanide (PHMB), cetyl pyridinium chloride, benzammonium chloride, benzalkonium chloride, and combinations thereof.

Suitable amphoteric surfactants include, for example, betaines, alkylamido betaines, sulfobetaines, N-alkyl betaines, sultaines, amphoacetates, amophodiacetates, imidazoline carboxylates, sarcosinates, acylamphoglycinates, such as cocamphocarboxyglycinates and acylamphopropionates, and combinations thereof. Specific examples of amphoteric surfactants include cocamidopropyl betaine, lauramidopropyl betaine, meadowfoamamidopropyl betaine, sodium cocoyl sarcosinate, sodium cocamphoacetate, disodium cocoamphodiacetate, ammonium cocoyl sarcosinate, sodium cocoamphopropionate, and combinations thereof.

Suitable zwitterionic surfactants include, for example, alkyl amine oxides, silicone amine oxides, and combinations thereof. Specific examples of suitable zwitterionic surfactants include, for example, 4-[N,N-di(2-hydroxyethyl)-N-octadecylammonio]-butane-1-carboxylate, S—[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable non-ionic surfactants include, for example, mono- and di-alkanolamides such as, for example, cocamide MEA and cocamide DEA, amine oxides, alkyl polyglucosides, ethoxylated silicones, ethoxylated alcohols, ethoxylated carboxylic acids, ethoxylated amines, ethoxylated amides, ethoxylated alkylolamides, ethoxylated alkylphenols, ethoxylated glyceryl esters, ethoxylated sorbitan esters, ethoxylated phosphate esters, glycol stearate, glyceryl stearate, and combinations thereof. It will be recognized by one skilled in the art that many of the nonionic surfactants described herein may act to improve the foaming properties of the cleansing composition of the multi-product care system, and may provide a more compact, reduced bubble size or creamy foam.

The cleansing composition may also include a thickener, which acts to thicken or increase the viscosity of the cleansing formulation. A variety of thickeners may be used in the cleansing compositions described herein. In one embodiment, the thickener may be a cellulosic thickener or gum. Examples of suitable cellulosic or gum thickeners include xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, hydroxypropylcellulose, hydroyethylcellulose, propylene glycol alginate, hydroxypropyl guar, amylopectin, cellulose gum, chitosan, modified chitosan, hydroxypropyl methylcellulose, microcrystalline cellulose, silica, fumed silica, colloidal silica, dehydroxanthan gum, non-acrylic based carbomers, and combinations thereof.

Alternately or in addition, the thickener may be an acrylic based polymer. Non-limiting examples of suitable acrylic based polymer thickeners include acrylates/C10-C30 alkyl acrylate crosspolymers, certain carbomers, acrylates copolymers, aminoacrylates copolymers, and combinations thereof. Examples of commercially available acrylic based polymer thickeners include Structure® Plus (Akzo Nobel, Pasadena, Calif.), which is an acrylates/aminoacrylates/C10-30 alkyl PEG-20 itaconate copolymer, Carbopol® Aqua SF-1 Polymer (Lubrizol Advanced Materials, Cleveland, Ohio), which is an acrylates copolymer, PEMULEN® TR-1 and TR-2 and Carbopol® ETD 2020 (available from Lubrizol Advanced Materials), which are acrylates/C10-30 alkyl acrylates crosspolymers, and the Carbopol® Ultrez series of polymers (available from Lubrizol Advanced Materials), which are carbomers.

Additional suitable agents for use in the cleansing composition may include humectants, preservatives, fragrances, chelating agents, and combinations thereof.

A skin care regime may further include a toning composition. Toning compositions provide such benefits as closing pores of a user's skin, restoring the natural pH of the skin (typically, a pH of from about 5.0 to about 5.5), removing skin impurities (e.g., dirt, oils, sebum, make-up, pollutants, and the like), hydrating the skin, and generally preparing the skin for treatment using a treatment composition, such as the anti-aging composition of the present disclosure, and/or an additional treatment composition as described below.

Generally, toning compositions for skin care include astringents, humectants, carriers, and combinations thereof. Suitable astringents include, for example, ethanol, witch hazel, rose water, alum, oatmeal, yarrow, bayberry, cold water, rubbing alcohol, astringent preparations such as silver nitrate, zinc oxide, zinc sulfate, Burow's solution, tincture of benzoin, and vegetable substances such as tannic and gallic acid, and combinations thereof. As used herein, the term "cold water" refers to water having a temperature below room temperature (approximately 25° C. (77° F.)).

Suitable humectants include, for example, glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, and urea. A particularly preferred humectant is glycerin.

Carriers for the toning compositions can be any carrier material typically known in the cosmetic and medical arts as a basis for ointments, lotions, creams, salves, aerosols, gels, suspensions, sprays, foams, and the like, and may be used in their art-established levels. In one particular embodiment, the carrier is an aqueous carrier. In another embodiment, the carrier is an alcohol carrier. The alcohol carrier can be any suitable alcohol. One particularly preferred alcohol is ethanol.

Other suitable carriers can also be used in the toning compositions. In certain embodiments, the carriers themselves can provide the skin care benefit. Non-limiting examples of suitable carriers include emollients, sterols or sterol derivatives, natural and synthetic fats or oils, polyols, surfactants, esters, silicones, and other pharmaceutically acceptable carrier materials.

In some embodiments, the skin care regimen includes a treatment composition for treating the skin in addition to the anti-aging composition of the present disclosure. Exemplary actives for the additional treatment composition may include actives that are known to have a treating effect on the skin such as improving the evenness of skin tone and reduction of acne. More specifically, the treatment agent can be selected from the group consisting of appearance modifying agents (e.g., exfoliating agents, skin-firming agents, anti-callous agents, anti-acne agents, wound care agents, enzyme agents, scar repair agents, humectant agents), therapeutic agents, pharmaceuticals (e.g., drugs, anti-oxidants, transdermal drug delivery agents, botanical extracts, vitamins, magnets, magnetic metals, and foods), xenobiotics, skin coloration agents (e.g., tanning agents, lightening agents, and brightening agents, shine control agents and drugs), shine control agents, colorant agents, surface conditioning agents (e.g., pH adjusting agents, moisturizers, skin conditioners, exfoliation agents, shaving lubricants, anti-callous agents, anti-acne agents, anti-aging agents, wound care agents, skin lipids, enzymes, scar care agents, humectants, powders, botanical extracts, and drugs) external analgesic agents, anti-inflammatory (e.g., anti-irritant agents, anti-allergy agents, wound care agents, transdermal drug delivery, and drugs), fragrances, odor neutralizing agents, soothing agents, calming agents, botanical extracts (e.g., peppermint oil, eucalyptol, *eucalyptus* oil, camphor, and tea tree oil), peptides, natural and synthetic fats or oils, moisture absorbers, and combinations thereof.

In one embodiment, in addition to the compositions described above, the skin care regimen includes a finishing composition. As with the other compositions, it should be understood that the various active ingredients described herein can be used in any of the products of the multi-product care regimen without departing from the scope of the disclosure.

When included, a finishing composition comprises a finishing agent that typically delivers moisturization, skin protection, or a moisture-barrier for sealing in moisture to the user. Specifically, the finishing agent can be any moisturizing agent, skin protectant, and/or moisture-barrier enhancing agent known in the art.

Additionally, the finishing agent may be capable of providing aesthetic benefits such as skin smoothing or a powdery feel. Examples of additional suitable finishing agents include skin conditioning agents (e.g., pH adjusting agents, moisturizers, skin conditioners, exfoliation agents, shaving lubricants, skin-firming agents, anti-callous agents, anti-acne agents, anti-aging agents, anti-wrinkle agents, anti-dandruff agents, wound care agents, skin lipids, enzymes, scar care agents, humectants, powders, botanical extracts, and drugs), fragrances, botanical extracts, powders, and combinations thereof.

It should be understood that the various active ingredients can be used in any of the products of the multi-product care regimen without departing from the scope of the disclosure. The specific active ingredients of the various products will depend upon the end daily regimen desired.

It should be understood by a skilled artisan that, while skin care systems will be discussed herein, regimes using the compositions of the present disclosure can be used for various other daily regimens comprising steps to cleanse, treat, moisturize and protect the skin. It is understood that skin care regimens can combine all of these steps, some of these steps, or have multiple iterations of the same steps so as to provide desired benefits to the skin.

This written description uses examples to disclose the invention, including the best mode, and also to enable any person skilled in the art to practice the invention, including making and using the compositions and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The disclosure will be more fully understood upon consideration of the following non-limiting Examples.

Example 1

Cell Survival

In this Example, a cell survival test was conducted to test for cytotoxicity of active ingredients.

Specifically, human dermal fibroblasts (HDFs) were exposed for 24 hours to growth media (DMEM+10% FBS) containing 0.5, 1, 2 and 5% v/v of active ingredients. Particularly, the active ingredients included ADIPOFILL'IN™ from Lucas Meyer Cosmetics (Quebec, Canada), ECOSAMBA™ PRO ("ECOSAMBA") from Chemyunion Quimica LTDA (Sorocaba, Brazil), ECOBIDENS™ from Chemyunion Quimica Ltd. (Sao Paulo, Brazil), and KOMBUCHKA™ from Sederma, France. After 24 hours exposure, MTT solution (thiazolyl blue tetrazolium blue) was added to cell culture wells for 2-4 hours at 37° C. MTT solution was then removed and isopropyl alcohol was added and incubated overnight at room temperature in the dark. Wells were measured at OD570 and compared to untreated control cells to determine cell viability.

As demonstrated in FIG. 1, none of the tested active ingredients significantly reduced cellular viability, nor did any significantly produce IL1-alpha, pro-inflammatory cytokine.

Example 2

Adipogenesis and Lipid/Free Fatty Acid Accumulation

In this Example, cells were exposed to active ingredients to study differentiation along the adipocyte lineage as evidenced by the lipid/free fatty acid accumulation in cells as detected by Oil Red-O staining.

Figure 2A:
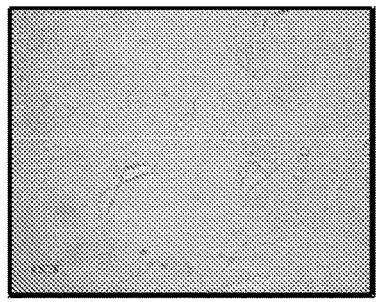
FIGS. 2A-2F are photomicrographs of mouse 3T3-L1 cells showing Oil Red-O staining after treatment of cells with various concentrations of active ingredients, as discussed in Example 2.
Figure 2B:
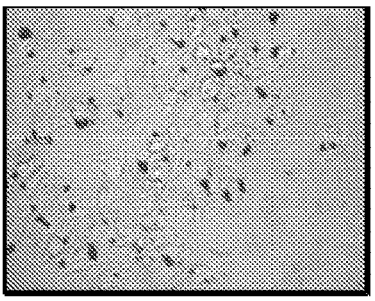
Figure 3A:
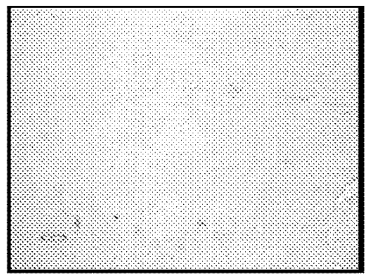
FIGS. 3A-3F are photomicrographs of human adipose derived stem cells showing Oil Red-O staining after treatment of cells with various concentrations of active ingredients, as discussed in Example 2.
Figure 3B:
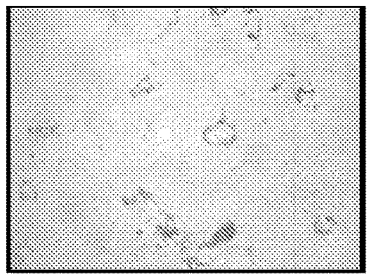

Specifically, mouse 3T3-L1 and human adipose-derived stem cells (ADSC) were exposed to 1% (v/v) active ingredients for 48 hours. Following 48 hours of exposure, standard growth media (MesenPro RS™ medium with 200 mm of L-glutamine and 10 mg/ml of gentamycin) was added and re-fed every 2-3 days to allow for differentiation along the adipose lineage for 2 weeks using the respective manufacturers' guidelines. For mouse 3T3-L1 cells, a positive control (FIG. 2B) was stimulated with DMEM (Dulbecco's Modified Eagle Medium) with 10% fetal bovine serum (FBS) and 5% penicillin/streptomycin and further supplemented with 1 μM dexamethasone, 0.5 mM IBMX and 10 μg/mL insulin. ADSC cells were differentiated with STEMPRO® Adipogenesis Differentiation Kit (Invitrogen, Carlsbad, Calif.) for a positive control (FIG. 3B).

Following 48 hours of exposure to active ingredients and the 2-week growth period, cells were fixed with 10% formalin for at least 1 hour. Formalin was removed and wells were washed with 60% isopropanol. Wells were then air dried completely. Oil Red-O working solution (filtered 0.21%) was added to each well and incubated for 10 minutes. Wells were washed under running water. Cells were imaged using a Leica DMIRB microscope at 400× magnification.

Figure 2C:
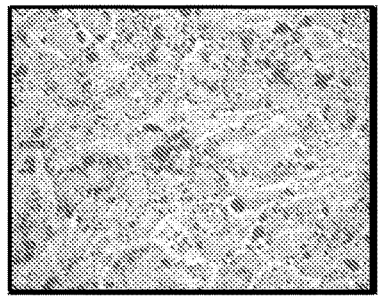
Figure 2D:
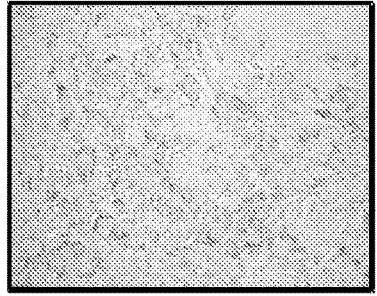
Figure 2E:
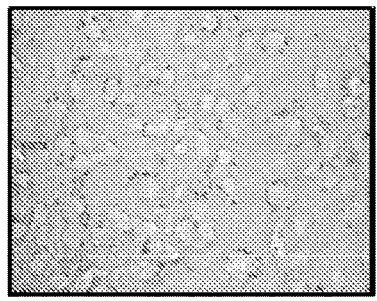
Figure 2F:
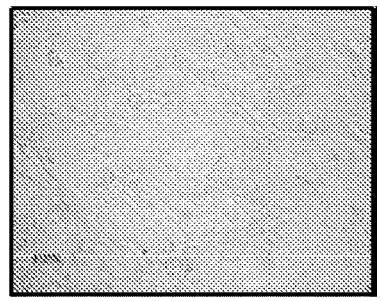
Figure 3C:
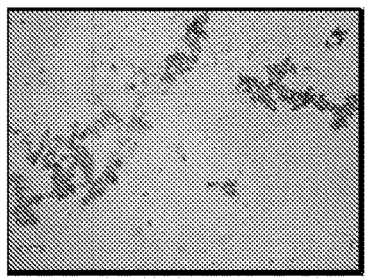
Figure 3D:
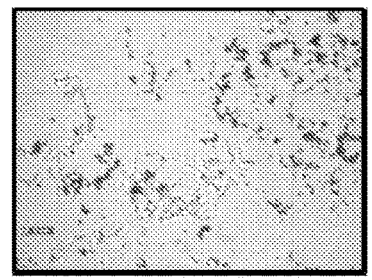
Figure 3E:
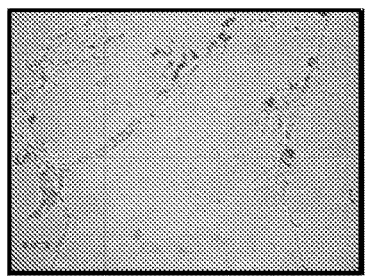
Figure 3F:
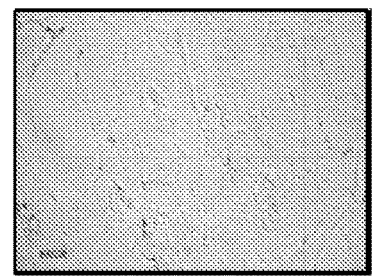

As demonstrated in FIGS. 2C and 2D, differentiated mouse 3T3-L1 cells exposed to ADIPOFILL'IN™ and ECOBIDENS™ extracts stained red (as shown, became darker in color) and became more round in shape, indicating that intracellular fatty acid content increased. Similar results were obtained in human ADSC cells (see, FIGS. 3C and 3D). Minimal staining was observed in either cell line stimulated with ECOSAMBA PRO™ or KOMBUCHKA™ (see FIGS. 2E, 2F, 3E, and 3F). Negative controls (untreated cells) were unstained and appeared elongated in shape (see, FIG. 2A and FIG. 3A). Positive controls were also stained and became more rounded in shape (see, FIG. 2B and FIG. 3B).

Example 3

Free Fatty Acid Quantification

In this Example, free fatty acid production in cells treated with various active ingredients was quantified by measuring free fatty acids in cultured media (MesenPro RS™ medium with 200 mM of L-glutamine and 10 mg/ml of gentamycin) following cell lysis.

Human adipocyte-derived stem cells (ADSC) were treated with 1% (v/v) active ingredients for 24 hours, followed by a 2-week growth period. Following ADSC lysis and prior to gene expression analysis (described below), free fatty acids were measured fluorometrically using a free fatty acid quantification kit according to the manufacturer's instructions (Abcam; Cambridge, Mass.). Positive control cells were differentiated with STEMPRO® Adipogenesis Differentiation Kit (Invitrogen, Carlsbad, Calif.).

Figure 4:
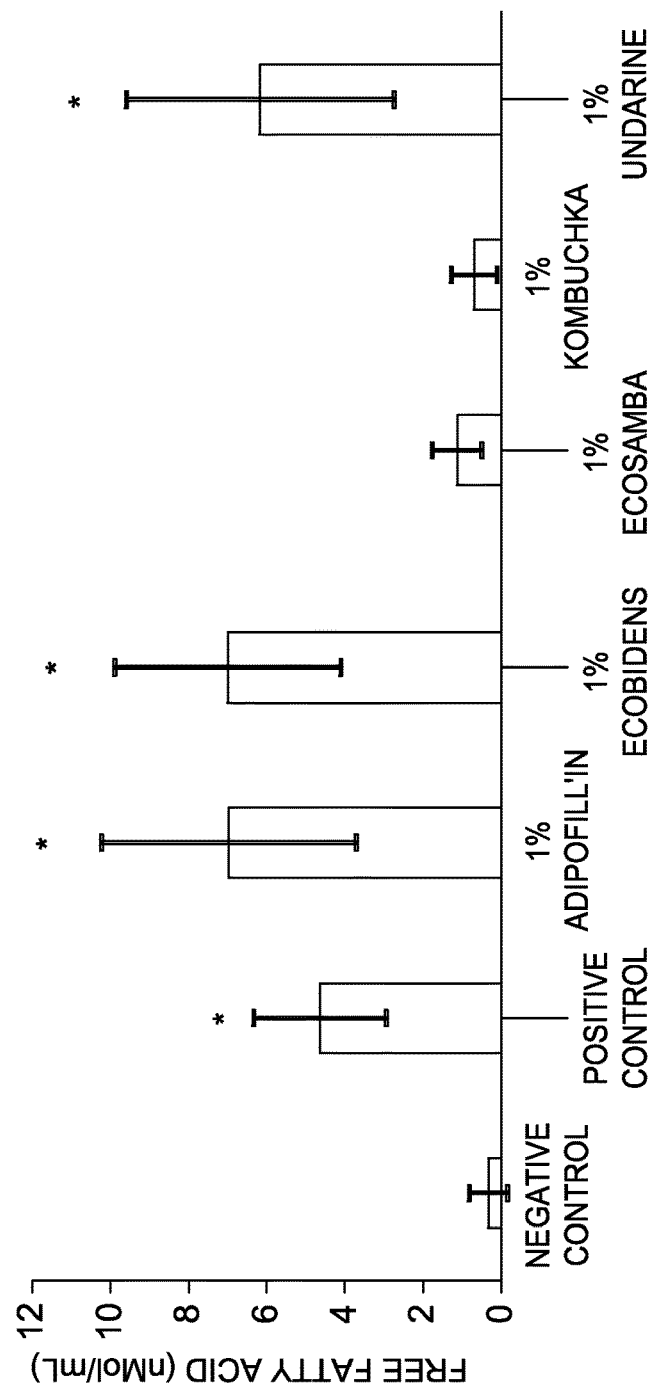
FIG. 4 is a graphical illustration showing free fatty acid production after treatment of cells with various concentrations of active ingredients, as discussed in Example 3. *$P<0.05$ by Student's T test to negative control, N=4. Data represents mean with standard deviation.

As shown in FIG. 4, 1% ADIPOFILL'IN™ (including propanediol, ornithine, phospholipids and glycolipids, commercially available from Lucas Meyer Cosmetics (Quebec, Canada)), 1% ECOBIDENS™, and 1% UNDARINE™ had a significant effect on the production of free fatty acids as compared to the negative control. ECOSAMBA™ (commercially available as ECOSAMBA™ PRO from Chemyunion Quimica LTDA (Sorocaba, Brazil)) and KOMBUCHKA™ (commercially available from Sederma, France), however, had a minimal effect on free fatty acid production.

Example 4

Genetic Marker Analysis

In this Example, qRT-PCR was used to measure expression of genes involved in adipogenesis.

PPAR-gamma is involved in adipogenesis signaling cascades as a known adipogenesis promoter. To investigate the expression of PPAR-gamma in adipogenesis stimulation via the active ingredients, RNA was isolated from treated ADSCs for qRT-PCR analysis. Relative expression of PPAR-gamma was compared to β-Actin (a housekeeping gene) and all samples were normalized to a negative control (untreated cells). Positive control cells were differentiated with STEMPRO® Adipogenesis Differentiation Kit (Invitrogen, Carlsbad, Calif.).

RNA was isolated from differentiated cells according to the manufacturer's instructions (QIAGEN RNeasy kit). cDNA was generated using QIAGEN First Strand Reverse Transcriptase kit according to the manufacturer's directions. TaqMan 2× Universal Master Mix with TaqMan GAPDH (VIC), β-Actin (VIC), and PPAR-gamma (FAM) validated probes were used to quantify relative expression to negative control. Delta-Delta cycle threshold (ΔΔCT) method was used for comparative analysis.

Figure 5:
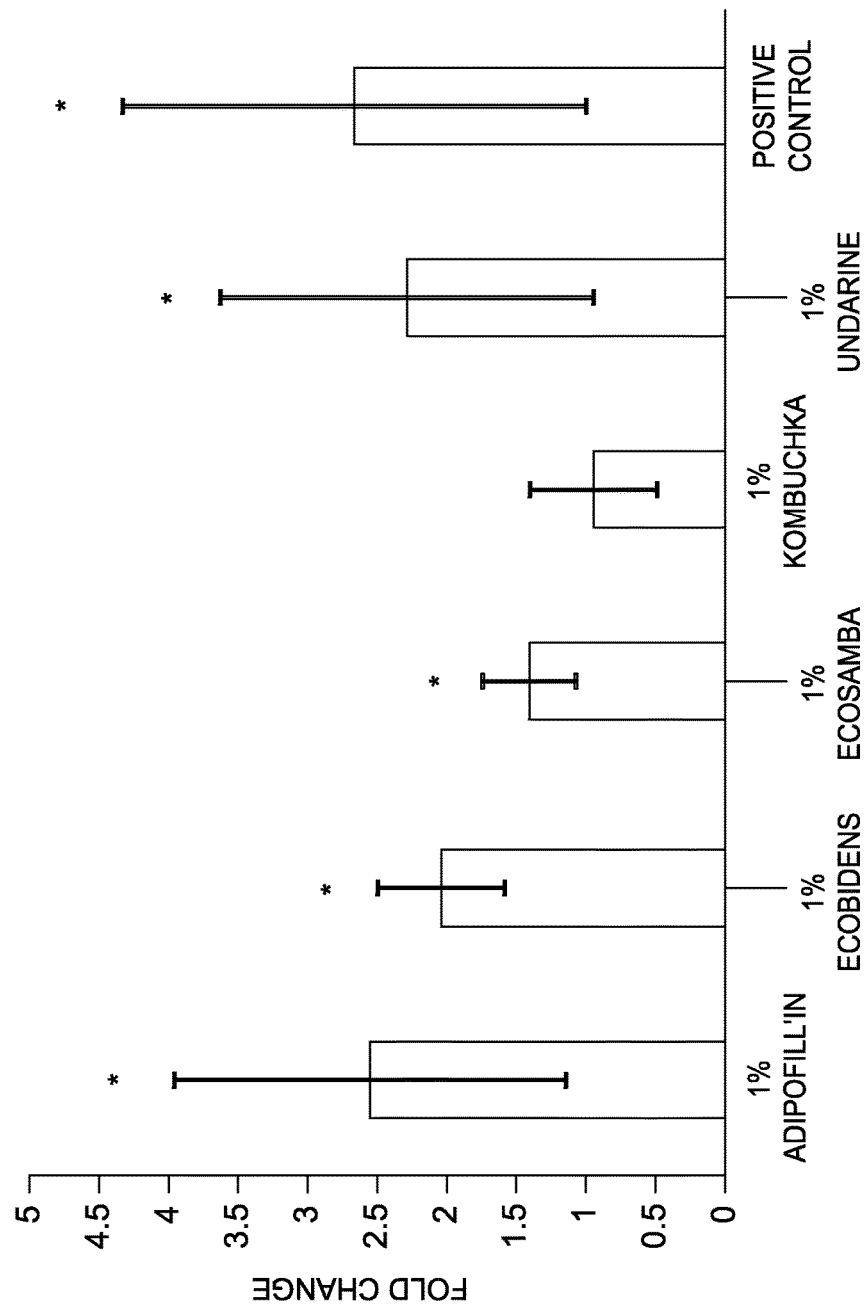
FIG. 5 is a graphical illustration showing expression of PPAR-gamma adipogenesis promoter after treatment of cells with various active ingredients, as discussed in Example 4. *$P<0.05$ by Student's T test to negative control, N=3. Data represents mean with standard deviation.

As shown in FIG. 5, a significant upregulation of PPAR-gamma was observed in cells treated with ADIPOFILL'IN™, ECOBIDENS™, ECOSAMBA™, and UNDARINE™.

Example 5

In this Example, actives were tested for effect on cell proliferation.

Specifically, human dermal fibroblasts were stained with carboxyfluorescein succinimidyl ester (CFSE) prior to treatment with ADIPOFILL'IN™, ECOBIDENS™, ECOSAMBA PRO™, KOMBUCHKA™, Undaria extract (UNDARINE™) or the combination of ADIPOFILL'IN™/ECOSAMBA PRO™. To establish a proliferation index, cells were measured at 0 hour, 24 hours, 48 hours and 96 hours.

Figure 6:
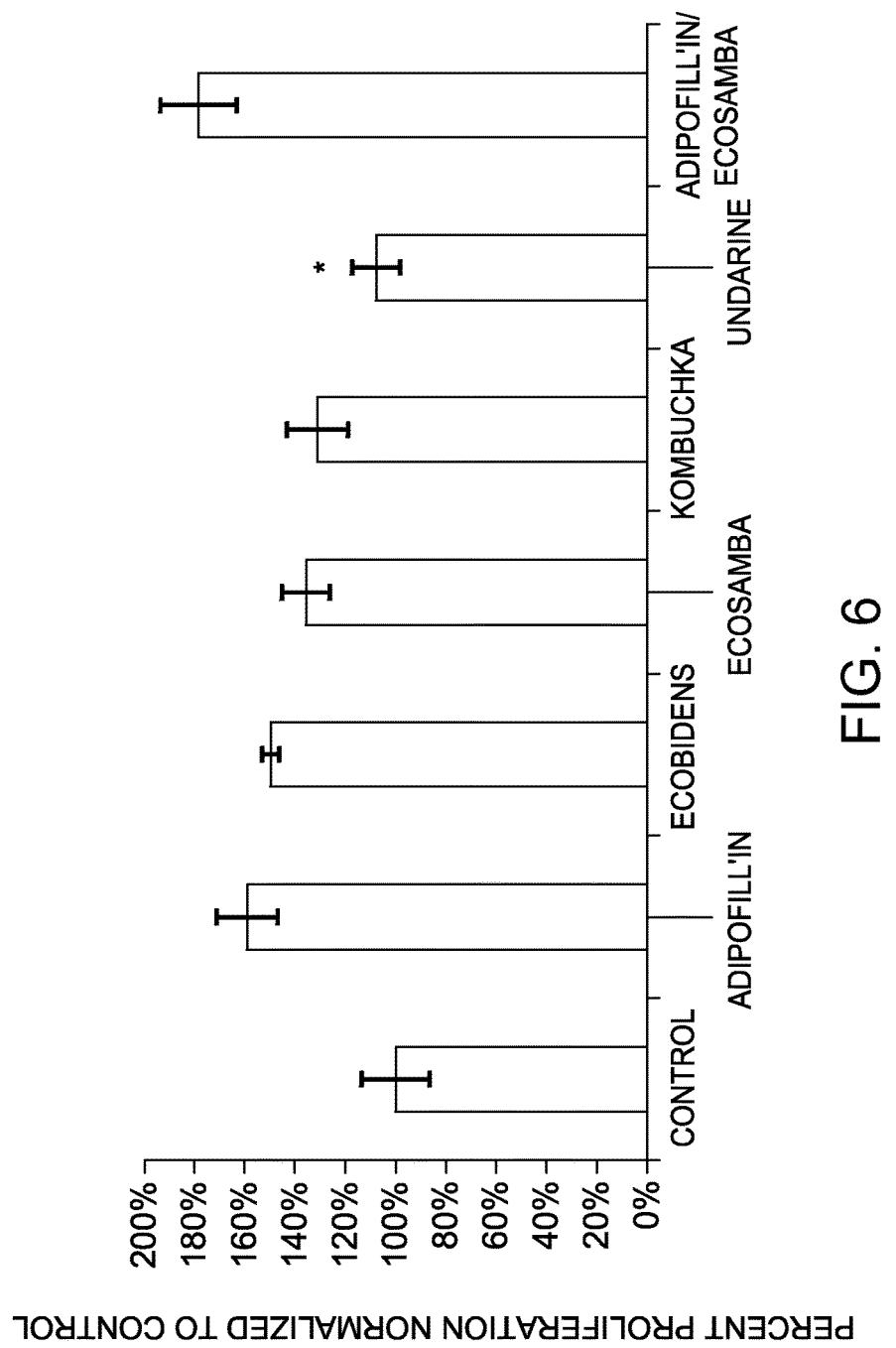
FIG. 6 is a graphical illustration showing percent cellular proliferation of human dermal fibroblasts following treatment with active ingredients, as discussed in Example 5.

As shown in FIG. 6, all of the actives except UNDARINE™ induced significantly greater cellular proliferation as compared to a control (untreated cells). Further, the combination of ADIPOFILL'IN™/ECOSAMBA PRO™ resulted in the greatest increase in fibroblast proliferation (see, FIG. 6) showing that this combination provides this additional benefit.

With respect to the sample treated with UNDARINE™, it is believed that the increased proliferation of fibroblasts involves a separate cellular pathway from adipogenesis and/or lipogenesis involving adipocytes. That is, this Example demonstrates that these actives affect a fibroblast-based pathway, which is separate from the pathway involving adipocytes.

Example 6

In this Example, combinations of actives were tested for stimulating adipogenesis.

Specifically, based on the discovery that ADIPOFILL'IN™ appeared to simulate adipogenesis via a different pathway than the other active agents, ADIPOFILL'IN™ was combined with ECOSAMBA PRO™. ADSC were treated with 0.5% (v/v) ADIPOFILL'IN™, 0.5% (v/v) ECOSAMBA PRO™ ("ECOSAMBA"), and a combination of 0.5% (v/v) ADIPOFILL'IN™ and 0.5% (v/v) ECOSAMBA PRO™. Cells were treated and grown as described above and analyzed by Oil Red O staining. Cells were also analyzed by quantifying free fatty acids and PPAR-gamma expression as described above. Positive control cells were differentiated with STEMPRO® Adipogenesis Differentiation Kit (Invitrogen, Carlsbad, Calif.).

Figure 7A:
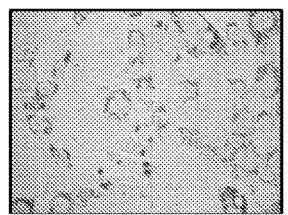
FIGS. 7A-7C are photomicrographs of ADSC stained with Oil Red-O following treatment with a formulation including water, propanediol and ornithine and phospholipids and glycolipids (A), a formulation including glycerin, *Spondias mombin, Mangifera* indicia and *Musa sapientum* (B) and a combination of a first formulation including water, propanediol and ornithine and phospholipids and glycolipids and a second formulation including glycerin, *Spondias mombin, Manifcra Mangifera* indicia and *Musa sapientum* (C) as discussed in Example 6.
Figure 7B:
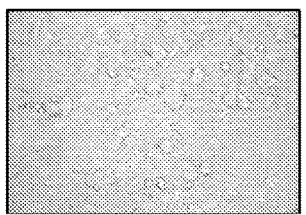
Figure 7C:
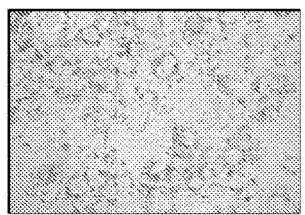

As shown in FIGS. 7A-7C, ADIPOFILL'IN™ and ECOSAMBA PRO™ acted synergistically in stimulating fatty acid production as visualized by Oil Red-O staining.

Figure 8:
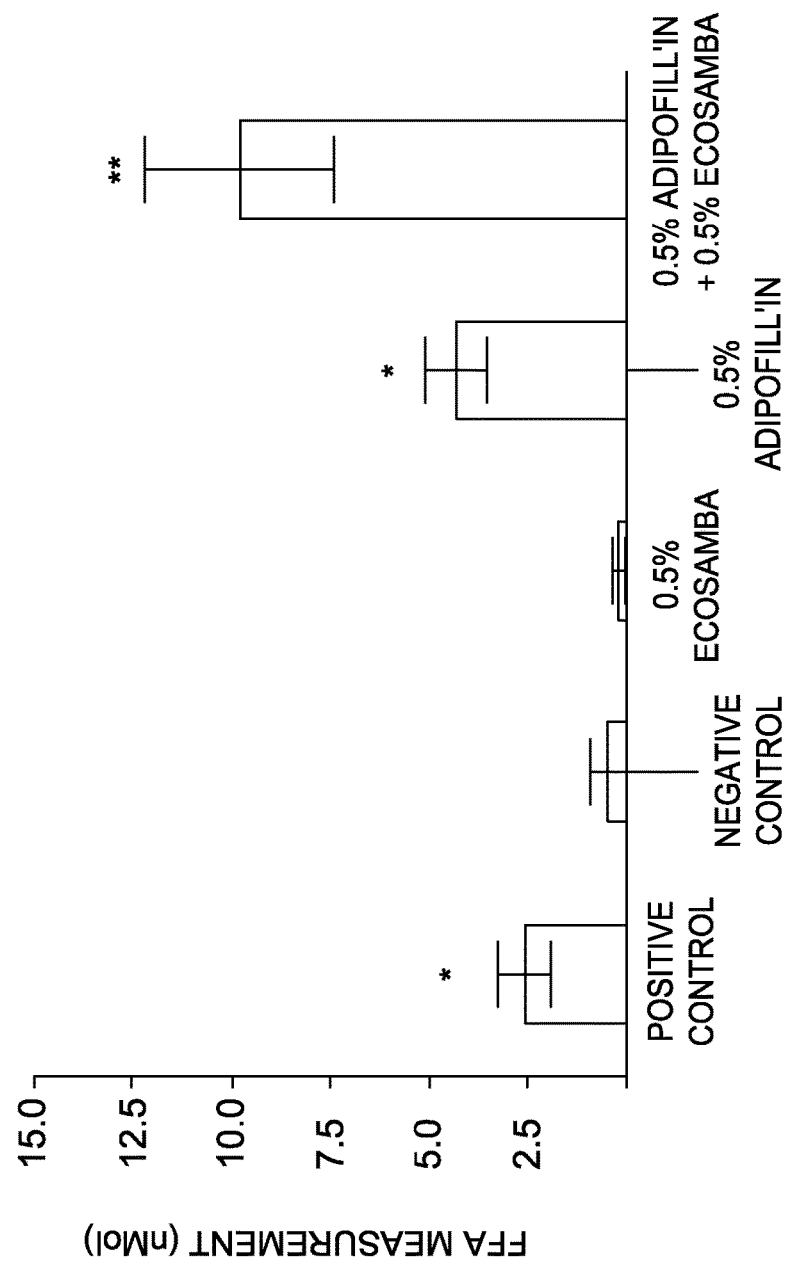
FIG. 8 is a graphical illustration showing free fatty acid production in ADSC following treatment with a formulation including water, propanediol and ornithine and phospholipids and glycolipids, a formulation including glycerin, *Spondias mombin, Mangifera indicia* and *Musa sapientum* and a combination of a first formulation including water, propanediol and ornithine and phospholipids and glycolipids and a second formulation including glycerin, *Spondias mombin, Mangifera indicia* and *Musa sapientum*, as discussed in Example 6. *$P<0.001$ by ANOVA, N=4. Data represents mean with standard deviation.
Figure 9:
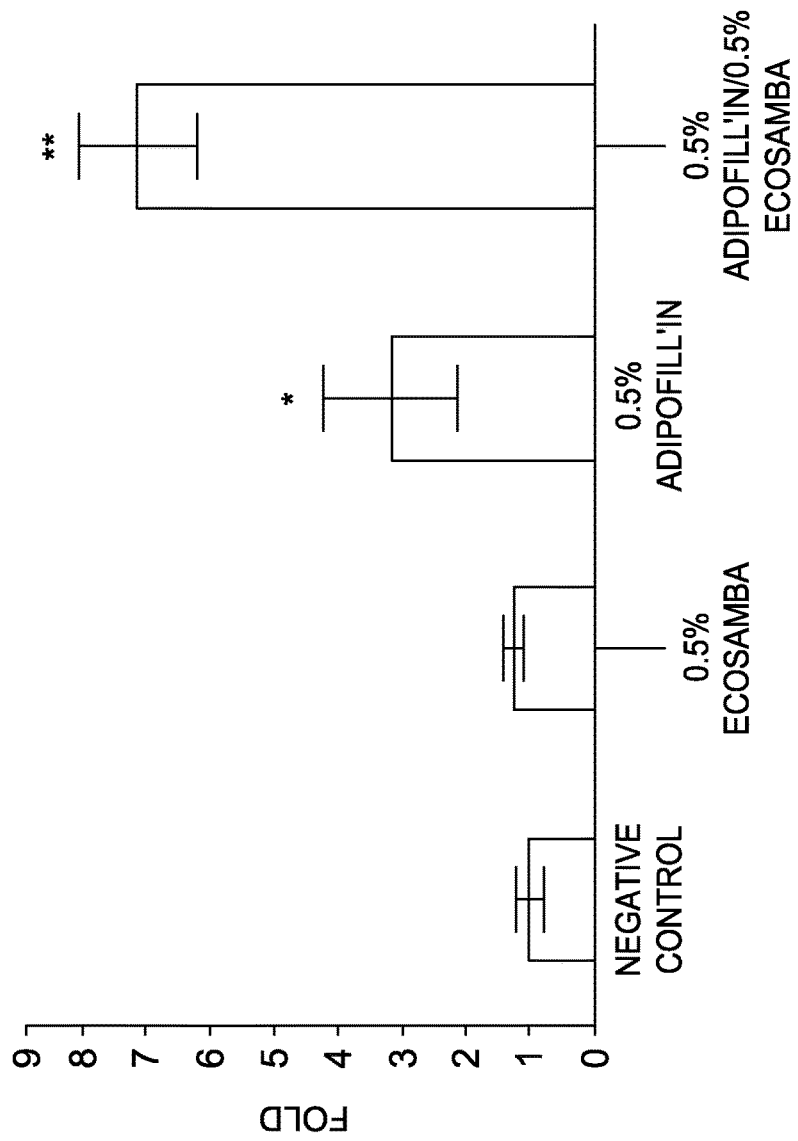
FIG. 9 is a graphical illustration showing relative expression of PPAR-gamma in ADSC following treatment with a formulation including water, propanediol and ornithine and phospholipids and glycolipids, a formulation including glycerin, *Spondias mombin, Mangifera indicia* and *Musa sapientum* and a combination of a first formulation including water, propanediol and ornithine and phospholipids and glycolipids and a second formulation including glycerin, *Spondias mombin, Mangifera indicia* and *Musa sapientum*, as discussed in Example 6. *$P<0.05$ by Student's T test, N=4. Data represents mean with standard deviation.

Further, the combination of ADIPOFILL'IN™ and ECOSAMBA PRO™ produced 10.0±0.6 nMol free fatty acids as compared to 5.0±0.5 nMol produced by ADIPOFILL'IN™ alone and 0.4±0.5 nMol produced by ECOSAMBA PRO™ alone, as shown in FIG. 8. As shown in FIG. 9, cells exposed to the combination of ADIPOFILL'IN™ and ECOSAMBA PRO™ exhibited a significant upregulation of PPAR-gamma. More particularly, the combination of 0.5% ADIPOFILL'IN™/0.5% ECOSAMBA PRO™ had 7.1 times more PPAR-gamma expression than a negative control (untreated cells). PPAR-gamma was 3.2 times more expressed in cells treated with 0.5% ADIPOFILL'IN™ than in the negative control. There was no significant expression of PPAR-gamma as compared to the negative control in cells treated with 0.5% ECOSAMBA PRO™ alone.

These results demonstrated that compositions including ADIPOFILL'IN™ and ECOSAMBA PRO™ targeting the adipose tissue underlying the skin can improve the overall fullness and appearance of aging skin. Surprisingly, the combination of ADIPOFILL'IN™ and ECOSAMBA PRO™ works synergistically to produce greater adipogenesis than when each ingredient was used alone. More particularly, the compositions and methods described herein can improve the overall fullness and appearance of aging skin by increasing adipocyte number and adipocyte lipid/free fatty acid production. The compositions and methods can improve the appearance of aging skin of the face and body. The compositions and methods can also improve the appearance of skin of the vulva and the labia, particularly in postmenopausal women.

Example 7

In these Examples, exemplary topical compositions were prepared with the following components:

TABLE 1

Gel formulation

| Trade Name | INCI | Wt % | Function |
|---|---|---|---|
| A | | | |
| Water | Water | 67.49 | Carrier |
| Carbopol Ultrez 21 | Carbomer | 1 | Hydrophilic Thickener |
| Disodium EDTA | Disodium EDTA | 0.01 | |
| Sodium Hydroxide | Sodium Hydroxide (10%) | q.a to pH 6.0 | |
| B | | | |
| SDA 40B Ethanol | Alcohol | 20 | Polar Co-Solvent |
| Polyderm PPI-G7/CA | Glycereth-7-Diglycerol-PEG-15 Cocamine/IPDI Copolymer | 0.5 | |
| ADIPOFILL'IN ™ | Propanediol, L-ornithine, phospholipids, glycolipids | 2 | Active |
| ECOSAMBA PRO | Spondias mombin pulp extract, Mangifera indica (Mango) pulp extract, Musa sapientum (Banana) pulp extract | 5 | Active |
| Glycerin | Glycerin | 2 | Carrier |
| Propylene Glycol | Propylene Glycol | 2 | Penetration Enhancer |
| TOTAL | | 100 | |

TABLE 2

Oil-Free Serum Formulation

| Trade Name | INCI Name | Wt. % | Function |
|---|---|---|---|
| Water | Water | 85.4 | Carrier |
| Structure Solanace | Potato Starch Modified | 3 | Hydrophilic Thickener |
| Simulgreen | Hydroxystearyl Alcohol, Hydroxystearyl Glucoside | 1 | |
| NaOH 10% | Sodium Hydroxide | q.s | |
| Zemea | Propanediol | 1 | Polar Co-Solvent |
| ADIPOFILL'IN ™ | Propanediol, L-ornithine, phospholipids, glycolipids | 2 | Active |
| ECOSAMBA PRO | Spondias mombin pulp extract, Mangifera indica (Mango) pulp extract, Musa sapientum (Banana) pulp extract | 2 | Active |
| Arlasolv DMI | Dimethyl Isosorbide | 0.5 | Penetration Enhancer |
| Floraesters K-20W Jojoba | Hydrolyzed Jojoba Esters, Water | 0.5 | |
| SymDiol 68 | 1,2-Hexanediol, Caprylyl Glycol | 1 | |
| Glycerox 767 | PEG-6 Caprylic/Capric Glycerides | 1.5 | |
| Fragrance | Fragrance | 0.1 | |
| DryFlo Elite LL | Aluminum Starch Octenylsuccinate and Lauroyl Lysine | 2 | |
| Total: | | 100 | |

TABLE 3

Oil in Water Emulsion

| | INCI | Wt % | Function |
|---|---|---|---|
| Product A | | | |
| Water | Water/Aqua | 77.85 | Carrier |
| Arlasolve DMI | Dimethyl Isosorbide | 1 | Penetration Enhancer |
| Transcutol CG | Ethoxydiglycol | 1 | Polar Co-Solvent |
| Structure Solanace | Potato Starch Modified | 3 | Hydrophilic Thickener |
| Product B | | | |
| Olivem 1000 | Cetearyl Olivate, Sorbitan Olivate | 1 | |
| Velsan SC | Sorbitan Caprylate | 0.5 | |
| Silwax D226 | Cerotyl Dimethicone | 1 | |
| Behenyl Alcohol | Behenyl Alcohol | 1 | |
| Dermol 99 | Isononyl Isononanoate | 2 | |
| Crodamol STS | PPG-3 Benzyl Ether Myristate | 1.5 | |
| Tegosoft M | Isopropyl Myristate | 0.75 | |
| Stimutex | Spent Grain Wax, Triolein, Linoleic Acid, Triticum Vulgare (Wheat) Germ Oil, Palmitic Acid Behenic Acid, Beta-Sitosterol | 0.25 | |
| BHT | BHT | 0.05 | |
| Sitosterol 75MM | B-Sitosterol | 0.1 | Active |
| Product C | | | |
| Xiameter 200 100cst | Dimethicone | 1 | |
| ADIPOFILL'IN ™ | Propanediol, L-ornithine, phospholipids, glycolipids | 2 | Active |
| Geogard ECT | Benzyl Alcohol & Salicylic Acid & Glycerin & Sorbic Acid | 1 | |

TABLE 3-continued

Oil in Water Emulsion

| | INCI | Wt % | Function |
|---|---|---|---|
| ECOSAMBA PRO | Spondias mombin pulp extract, Mangifera indica (Mango) pulp extract, Musa sapientum (Banana) pulp extract | 5 | Active |
| Citric Acid | Citric Acid | q.a. to pH 5.5 | |
| Sodium Hydroxide | Sodium Hydroxide | q.a. to pH 5.5 | |

TABLE 4

Foaming Body Wash

| Trade Name | INCI Name | % Wt. | Function |
|---|---|---|---|
| Part A | | | |
| Water | Water/Aqua | 90.919 | Carrier |
| Tic Prehydrated Xanthan Gum | Xanthan Gum | 0.050 | Hydrophilic Thickener |
| Versene NA2 | Disodium EDTA | 0.100 | |
| Aloe Vera Powder 200x | Aloe Baradensis Leaf Juice | 0.010 | |
| L-Panthenol | Panthenol | 0.100 | |
| Sodium Benzoate, FCC | Sodium Benzoate | 0.450 | |
| Zemea prorandiol | 1,2-Propanediol | 1.500 | Polar Co-solvent |
| Glycerin, 99.7% | Glycerin | 1.000 | Penetration Enhancer |
| Mackam 35 UL HA | Cocamidopropyl Betaine | 3.000 | |
| Plantacare 2000 N UP | Decyl Glucoside | 1.000 | |
| Part B | | | |
| Sensiva SC 50 | Ethylhexylglycerine | 0.300 | |
| Tagat CH 60 | PEG-60 Hydrogenated Caster Oil | 0.750 | |
| Alkumuls SML 20 | Polysorbate 20 | 0.45 | |
| Sistosterol 75 MM | Beta- Sistosterol | 0.0015 | Active |
| Part C | | | |
| ECOSAMBA PRO | Spondias mombin pulp extract, Mangifera indica (Mango) pulp extract, Musa sapientum (Banana) pulp extract | 0.100 | Active |
| ADIPOFILL'IN ™ | Propanediol, L-ornithine, phospholipids, glycolipids | 0.100 | Active |
| US260085/00 (Aloe Fresh) | Fragrance | 0.100 | |
| 50% Citric Acid | Citric Acid, Water | 0.070 | |
| | Total | 100.000 | |

What is claimed is:

1. A topical composition comprising: from about 0.1% (w/w) to about 20% (w/w) of a first formulation and from about 0.1% (w/w) to about 20% (w/w) of a second formulation, wherein the first formulation comprises L-ornithine and wherein the second formulation comprises *Spondias mombin* pulp extract, *Mangifera indica* pulp extract and *Musa sapientum* pulp extract; wherein at least one of the first formulation and the second formulation further comprises a carrier selected from the group consisting of an ointment, a lotion, a cream, a salve, a gel, an emulsion, a solid stick, and combinations thereof.

2. The topical composition of claim 1 wherein the first formulation further comprises at least one of propanediol, phospholipids and glycolipids.

3. The topical composition of claim 1 wherein the second formulation further comprises glycerin.

4. The topical composition of claim 1, wherein at least one of the first formulation and the second formulation further comprises a hydrophilic carrier selected from the group consisting of water, glycerin, propylene glycol and combinations thereof.

5. The topical composition of claim 1 further comprising beta-sitosterol.

6. The topical composition of claim 5 wherein the composition comprises from about 0.001% (w/w) to about 10% (w/w) of beta-sitosterol.

7. The topical composition of claim 1 further comprising a skin penetration enhancer.

8. The topical composition of claim 7 wherein the skin penetration enhancer is selected from the group consisting of sulfoxides, alcohols, fatty acids, fatty acid esters, polyols, amides, surfactants, terpenes, alkanones, organic acids, and combinations thereof.

9. A topical composition comprising: from about 0.1% (w/w) to about 20% (w/w) of a first formulation and from about 0.1% (w/w) to about 20% (w/w) of a second formulation, wherein the first formulation comprises propanediol, L-ornithine, phospholipids, and glycolipids, and wherein the second formulation comprises water, glycerin, *Spondias mombin* pulp extract, *Mangifera indicia* pulp extract, *Musa sapientum* pulp extract, benzyl alcohol, and potassium sorbate; wherein at least one of the first formulation and the second formulation further comprises a carrier selected from the group consisting of an ointment, a lotion, a cream, a salve, a gel, an emulsion, a solid stick, and combinations thereof.

10. The topical composition of claim 9 further comprising beta-sitosterol.

11. The topical composition of claim 10 wherein the composition comprises from about 0.001% (w/w) to about 10% (w/w) of beta-sitosterol.

12. The topical composition of claim 9 further comprising a skin penetration enhancer.

13. The topical composition of claim 12 wherein the skin penetration enhancer is selected from the group consisting of sulfoxides, alcohols, fatty acids, fatty acid esters, polyols, amides, surfactants, terpenes, alkanones, organic acids, and combinations thereof.

14. The topical composition of claim 12 wherein the skin penetration enhancer is present in the composition in an amount of from about 0.01% (by weight of the composition) to about 25% (by weight of the composition).

15. The topical composition of claim 9 further comprising one or more of fragrances, scents, dyes, surfactants, rheology modifiers, and film formers.

16. The topical composition of claim 1 wherein the composition comprises from about 0.1% (w/w) to about 2% (w/w) of the first formulation.

17. The topical composition of claim 9 wherein the composition comprises from about 0.1% (w/w) to about 2% (w/w) of the first formulation.

18. The topical composition of claim 1 wherein the composition comprises from about 0.1% (w/w) to about 5% (w/w) of the second formulation.

19. The topical composition of claim 9 wherein the composition comprises from about 0.1% (w/w) to about 5% (w/w) of the second formulation.

20. The topical composition of claim 1 wherein the composition comprises about 2% (w/w) of the first formulation and about 5% (w/w) of the second formulation.

* * * * *